United States Patent [19]

Jimbo

[11] Patent Number: 4,742,718
[45] Date of Patent: May 10, 1988

[54] APPARATUS FOR MEASURING PARTICLE-SIZE DISTRIBUTION

[75] Inventor: Genji Jimbo, Nagoya, Japan

[73] Assignee: Onoda Cement Company, Ltd., Onoda, Japan

[21] Appl. No.: 922,862

[22] Filed: Oct. 24, 1986

[30] Foreign Application Priority Data

Oct. 29, 1985 [JP] Japan ................................ 60-241793
Oct. 29, 1985 [JP] Japan ................................ 60-241794

[51] Int. Cl.⁴ .......................................... G01N 15/02
[52] U.S. Cl. .................................................. 73/865.5
[58] Field of Search ...................... 73/865.5, 438, 714, 73/438

[56] References Cited

U.S. PATENT DOCUMENTS

| | | | |
|---|---|---|---|
| 1,969,081 | 8/1934 | Vogel-Jurgensen | 73/865.5 |
| 3,206,983 | 9/1965 | Muschelknautz | 73/865.5 |
| 3,208,286 | 9/1965 | Richard | 73/865.5 |
| 3,788,146 | 1/1974 | Hartman | 73/61.4 |
| 3,896,660 | 7/1975 | Valentyik | 73/438 |
| 4,175,426 | 11/1979 | Rosenblum | 73/61.4 |
| 4,287,757 | 9/1981 | Bucsky et al. | 73/865.5 |
| 4,307,609 | 12/1981 | Rosenblum | 73/438 |

FOREIGN PATENT DOCUMENTS

| | | | |
|---|---|---|---|
| 0155233 | 12/1980 | Japan | 73/438 |
| 2080548 | 2/1982 | United Kingdom | 73/865.5 |
| 0641317 | 1/1979 | U.S.S.R. | 73/438 |

Primary Examiner—Stewart J. Levy
Assistant Examiner—Robert R. Raevis
Attorney, Agent, or Firm—Price, Heneveld, Cooper, DeWitt & Litton

[57] ABSTRACT

An apparatus for measuring particle-size distribution which is constructed by arranging a measuring cell or cells in vertical direction, i.e. their longitudinal directions in alignment with the direction of the gravity, or mounting a measuring cell or cells on a rotor rotatable in a horizontal plane so that their longitudinal directions are in alignment with the radial directions as that of centrifugal force; inserting tips of a couple of pressure transmitting tubes having lengths different between them into each of said measuring cells; and securing base ends of said pressure transmitting tubes to a pressure-detecting unit. To operate this apparatus, a suspension of a powder to be measured is introduced into said measuring cell, particles of suspension in the measuring cell is made to settle by the gravity or a centrifugal force, the amount of powder between the tips of pressure transmitting tubes of said couple is determined by measuring the pressure difference between said tips, and the particle-size distribution is determined on the basis of the obtained amount of powder and a particle size calculated by Stokes' law from the settling time elapsed.

5 Claims, 4 Drawing Sheets

APPARATUS FOR MEASURING PARTICLE-SIZE DISTRIBUTION

BACKGROUND OF INVENTION

1. Field of the Invention

The present invention relates to an apparatus for measuring particle-size distribution of a powder which is used or produced in a powder industry, such as cement- and ceramics-industry.

2. Description of the Prior Art

The prior art apparatuses of this kind include a sieving apparatus, an apparatus wherein the sedimentation of a powder in a suspension having been formed by dispersing the powder in a liquid is detected by measuring the solid content in liquid, the specific gravity, or the intensity of transmitted light, an apparatus in which a dispersed powder is irradiated by a beam of light and the intensity of scattered light is measured, and an apparatus wherein a lazer beam is passed through a dispersed powder and the particle-size distribution is determined from the obtained diffraction pattern.

However, each of the aforementioned various apparatuses has some respective drawbacks. For instance, the sieving apparatus is employable at most for measuring particles of the extent of 5 $\mu$m and cannot be used in the recent technique which is required to have a measuring range extending to less than 0.1 $\mu$m. The method in which the solid content in liquid is detected suffers the inconvenience that the size of employable measuring cell cannot be diminished. In the apparatus where the sedimentation of particles is detected by the intensity of transmitted light, a part of incident light is absorbed by the liquid medium during passing through a suspension. An error in measuring due to an amount of such an absorption is usually corrected by multiplication of the measure by a correction factor called absorption coefficient, the absorption coefficient depending on the nature of used measuring apparatus. However, the validity of this correction is open to question. As for the apparatus where the intensity of scattered light or the diffraction pattern is employed, errors are brought about frequently in the measurement.

SUMMARY OF THE INVENTION

One object of this invention is to provide an apparatus for measuring particle-size distribution of a powder in which an error in measuring occurs scarcely, the accuracy in measurement is remarkable, and the operation thereof is quite easy.

Another object of the invention is to provide an apparatus for measuring particle-size distribution of a powder wherein the principle of measurement is quite clear and the measuring can be performed within a short period of time.

It has been found by this invention that the above objects may be accomplished by providing an apparatus for measuring particle-size distribution of a powder wich comprises a measuring cell for receiving a suspension of a powder to be measured, a couple of pressure transmitting tubes different in length, tips of said pressure transmitting tubes having been inserted from above in said measuring cell, and a pressure-detecting unit to which each of base ends of said pressure transmitting tubes is secured, said pressure-detecting unit being electrically connected with a measuring device.

BRIEF DESCRIPTION OF THE DRAWINGS

The advantages of the present invention will become apparent from the following detailed description of preferred embodiments thereof in connection with the accompanying drawings in which like numerals designate like elements and in which.

DESCRIPTION OF PREFERRED EMBODIMENTS

Figure 1:
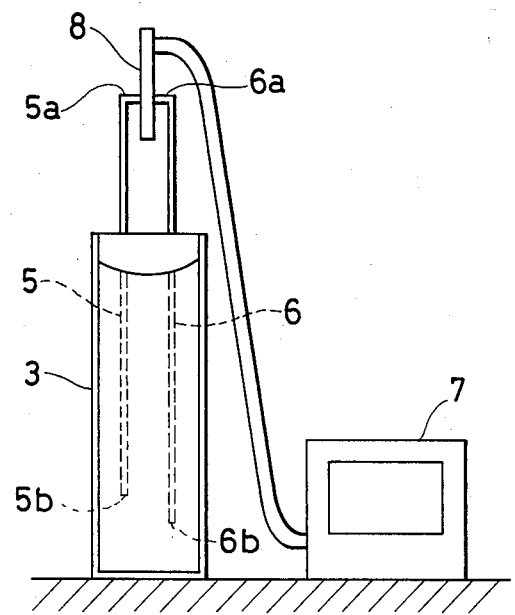
FIG. 1 is a schematic diagram of an apparatus for measuring particle-size distribution as one embodiment of the present invention.

The apparatus for measuring particle-size distribution of a powder shown in FIG. 1 comprises a measuring cells 3 for receiving a sample; a pair of pressure transmitting tubes 5 and 6 having individually different immersed depths; pressure-detecting units 8 secured to both base ends of said pressure transmitting tubes 5 and 6; and a measuring device 7 electrically connected with said pressure-detecting units 8.

Figure 2:
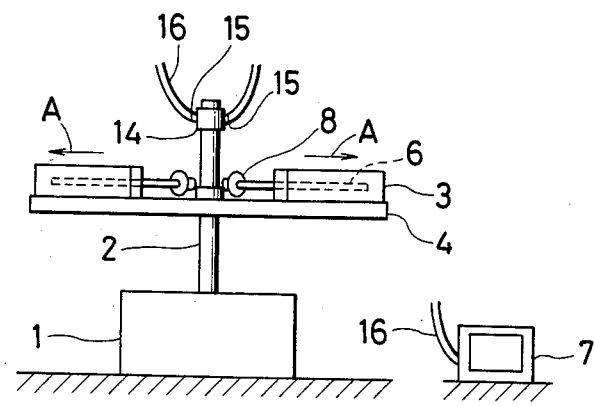
FIG. 2 is a schematic diagram of an apparatus for measuring particle-size distribution as another embodiment of this invention.
Figure 3:
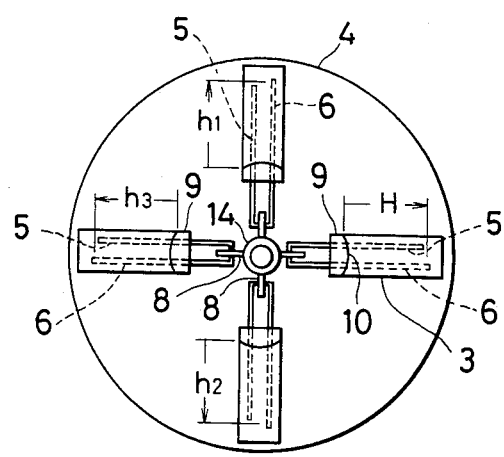
FIG. 3 shows a plan view of a part of the apparatus shown in FIG. 2.
Figure 4:
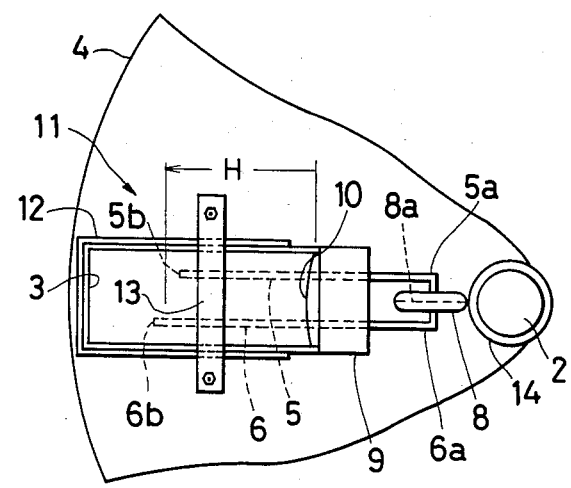
FIG. 4 is enlarged plan view for representing in detail a part of FIG. 3.
Figure 5:
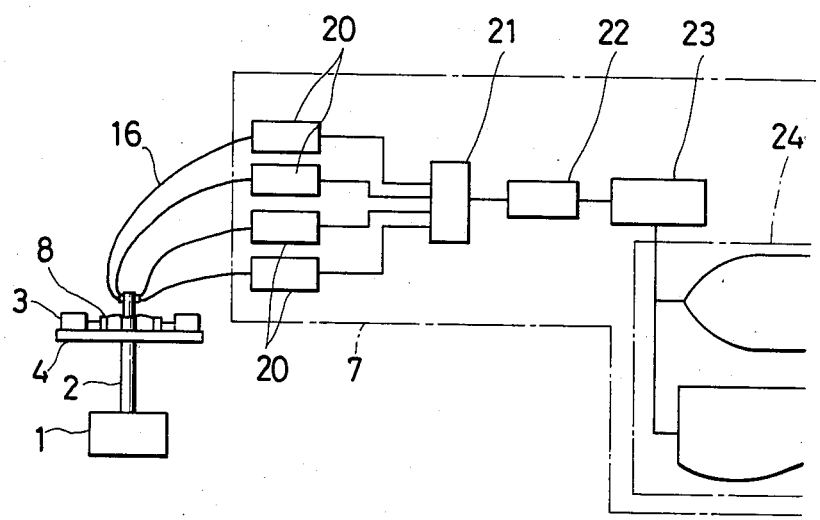
FIG. 5 is a block diagram of circuit in the apparatus shown in FIG. 2.

The apparatuses for measuring particle-size distribution of a powder shown in FIGS. 2-4 comprises a rotating axis 2 connected with a driving unit 1; a rotor 4 mounted on said rotating axis 2; a measuring cells 3 for receiving a sample to be measured; fixing members 11 for fixing said measuring cell 3 to the rotor so that its longitudinal direction may coincide with the radial direction of the rotor; couples of pressure transmitting tubes 5 and 6 having immersed depths different therebetween; pressure-detecting units 8 secured to both base ends of said pressure transmitting tubes 5 and 6; and a measuring device 7 electrically connected with said pressure-detecting units 8.

A sample of a powder to be measured is dispersed in a liquid to form a suspension. The obtained suspension is introduced into a measuring cell. In the case of the apparatus shown in FIG. 1, suspended particles are allowed to settle as a result of gravity. In the case of the apparatus shown in FIGS. 2-4, the rotor 4 revolves when the driving unit 1 is started to drive the rotating axis 2. The measuring cells 3 are rotated. Thus, the suspension in measuring cell 3 is subjected to a centrifugal force and suspended particles in the suspension begin a centrifugal sedimentation in the direction of arrow A. In the case of the apparatus shown in FIG. 1 as well as that shown in FIGS. 2-4, coarser particles settle rapidly and finer particles settle slowly, although the mean speed of settling is different between two apparatuses.

Now, suspended particles contained in a thin zone at a certain depth in the measuring cell 3 are considered. In the course of time, particles settle down to the specified zone from the upper part of the measuring cell and at the same time particles settle down from the specified zone to the lower part of the measuring cell. At first, these two are in equilibrium, while after a certain period, when all of the particles coarser than a certain size have disappeared from the upper part of the measuring cell and no longer settle into the specified zone, the total weight of particles in said zone starts to decrease. The decrease in the total weight of particles in the zone corresponds to the total weight of particles having a certain diameter, which have disappeared from the zone. The period of time required for the disappearance of particles having a certain diameter at a certain depth, i.e. the period of time required for said particles to fall from the uppermost position to said depth, is numerically determined by Stokes' law. Conversely, the diameter of said particles can be calculated from the settling time.

Accordingly, a particle-size distribution can be obtained when the relation between the total weight of particles existing at a certain depth and the settling time is measured. Static pressures in a suspension contained in the measuring cell 3 are transmitted through pressure transmitting tubes 5 and 6 to the pressure-detecting unit 8 secured both to base ends 5a and 6a of tubes 5 and 6. A difference between the pressure at the tip 5b of tube 5 and that at the tip 6b of tube 6 having a length different from that of tube 5 is sensed by the pressure-detecting unit 8. As the aforementioned pressure difference varies depending on the amount of powder in suspension which exists between the tip 5b of tube 5 and the tip 6b of tube 6, the weight of powder existing between the tip 5b and the tip 6b can be measured by virtue of said pressure difference. The pressure difference sensed by pressure-detecting unit 8 is taken out as an electric signal and the signal is transmitted to the measuring device 7 which is electrically connected with the pressure-detecting unit 8. Thus, the particle-size distribution is determined on the basis of the diameter of particle referred to above and the pressure difference.

The rotor 4 mentioned above is formed to be a disc and plural measuring cells 3 are provided in alignment with the radius of disc. The pressure transmitting tubes 5 and 6 are detachably mounted on the measuring cell 3. In addition, the pressure transmitting tubes 5 and 6 consist of a couple of thin tubes of which parts inserted into the measuring cell 3 are different in length. The length of inserted part can be selected as desired. Further, each of base ends 5a and 6a of pressure transmitting tubes 5 and 6 is formed to be an integral part of pressure-detecting unit 8, as shown by FIGS. 2-4. The pressure transmitting tubes are filled with a liquid for transmitting pressure.

Usually, the pressure sensor of pressure-detecting unit 8 detects a displacement of a pressure sensitive membrane 8a. In order to prevent any deformation of membrane due to the centrifugal force, the pressure sensitive membrane 8a is disposed near the rotating axis and is so arranged that the membrane and the axis of rotation of the rotor lie in one and the same plane.

Measuring cell 3 is disposed in a peripheral part of rotor 4 where the centrifugal force is intense in order to promote the sedimentation of particles in the suspension. As the pressure transmitting tubes 5 and 6 and the measuring cell 3 are formed to be detachable from each other, the procedure for introducing a suspension into the measuring cell 3 is facilitated.

Specifically, a closure 9 is so shaped that a part thereof is fitted in the measuring cell 3 and the pressure transmitting tubes 5 and 6 penetrate therethrough. The inner surface of closure 9 is made to be a convex face 10. When the closure with this shape is fitted into the measuring cell 3 filled with a suspension, air on the suspension is excluded and the measuring cell 3 can be hermetically sealed. The closure 9 is made of an elastomeric material, or, alternatively, a sealing compound, such as grease, may be applied thereto for the same purpose. As a result of such an exclusion of air from the suspension, any generation of cavitation can be inhibited within the pressure transmitting tubes 5 and 6 and the pressure-detecting unit 8. In FIG. 4 illustrating a part of FIG. 3 in detail, reference numeral 11 designates a fixing member for securing a measuring cell 3 to rotor 4. Reference numerals 12 and 13 designate a frame member and a fixing band, respectively, both a part of said fixing member. In FIG. 2, reference numerals 14, 15 and 16 designate a slip ring, a brush and a lead wire, respectively. The pressure transmitting tubes 5 and 6 are filled with a clean liquid. Usually, the same liquid with the medium liquid of the suspension to be measured is used. And, it is required that the liquid in the pressure transmitting tube forms a continuous junction with the suspension to be measured when the pressure transmitting tubes 5 and 6 are inserted in the measuring cell 3. Because of this requirement, the diameter of pressure transmitting tubes 5 and 6 is restricted. That is to say, the tips 5b and 6b, as detecting element of pressure, of pressure transmitting tubes 5 and 6 must be formed to be of such small size that the filling liquid forms a convex surface to the atmosphere. For example, the pressure transmitting tube is made to have a diameter of 3.5 mm or less when the filling liquid is distilled water. If the tube is made to have a diameter larger than this value, the surface of filling liquid forms a concave when viewed from the outside, i.e. so-called meniscus. When this is the case, the transmission of pressure cannot be conducted and the measurement cannot be performed.

When a liquid without pre-degassing treatment, is used as filling liquid, air dissolved in it may be evolved during measurement and the transmission of pressure may become difficult. Accordingly, it is preferred that a liquid to be used is sufficiently pre-degassed or an oil, e.g. a silicone oil, in which air can hardly be dissolved is employed as medium liquid.

The above description is of the case in which the particle-size distribution of a powder is determined by employing only one measuring cell. That is to say, the pressure difference between certain two depths in a measuring cell is measured as settling proceeds. However, the measuring apparatus of this invention is so constructed that a plurality of measuring cells can be employed and the measured values can be obtained almost simultaneously to enhance the precision of measurement.

Now, the measurement with plural measuring cells will be described in the following. First, measuring cells 3 are dismounted from frame members 12. Aliquots of a suspension which has been prepared in advance by dispersing a powder to be measured in a liquid are introduced in measuring cells 3. Each length of pressure transmitting tubes 5 and 6 is suitably selected and the tubes are mounted on measuring cells by fitting the closures 9 in the cell. When the driving unit 1 is actuated, particles of suspension in meauring cells begin to settle due to the centrifugal force. A pressure-detecting unit 8 detects a pressure difference between tips 5b and 6b of pressure transmitting tubes 5 and 6 at a suitably selected depth, e.g. $h_1$, of tube 6 in a measuring cell 3. Other pressure-detecting units 8 simultaneously detect the pressure differences at suitably selected depths $h_2$, $h_3$, etc. in other measuring cells 3, respectively.

As shown in FIGS. 2 and 4, each of thus-obtained measured values is taken out from the apparatus via slip ring 14, and is amplified by means of respective amplifier 20. Amplified values are sampled in a signal selecting part 21, is digitized in an analog/digital convertor 22, and is analyzed, calculated, and synthesized in a arithmetic unit 23 to obtain the desired particle-size distribution data. The obtained data is displayed by means of a display 24 or is printed out.

Further, although four measuring cells 3 are shown in FIG. 3, any number of measuring cells can be provided as desired.

As coarser particles fall rapidly and finer particles slowly as mentioned above when particles in suspension are moved in a centrifugal force field, coarser particles are concentrated in a part near the bottom and the portion of finer particles increases in a part near the closure. Consquently, to enhance the precision of the measurement, it is preferred that a pressure difference is detected by extending pressure transmitting tubes to a deep position on the part of coarser particles and by holding them at a position of little depth on the part of finer particles. Accordingly, couples of pressure transmitting tubes 5 and 6 having different inserted lengths are selected so as to reach the depths of $h_1$, $h_2$, $h_3$ etc., respectively, and said couples are inserted into the respective measuring cells 3. The measuring cells thus-prepared are employed and the pressure differences are separately measured in the separate detecting ranges. When these measured values are analyzed, calculated, and synthesized, a particle-size distribution of the whole can be obtained with excellent precision and within a short period of time.

Figure 6:
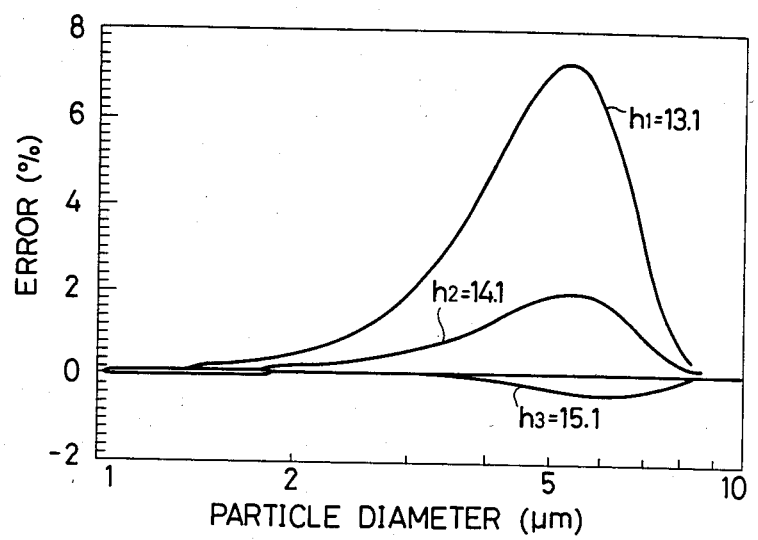
FIG. 6 represents a graph which shows an example of the result from measuring a powder-size distribution of a powder by means of an apparatus according to the present invention.

FIG. 6 illustrates ratios of error in measuring particle-size distribution in the case when the measurements are conducted at the inserted depths of $h_1$, $h_2$, and $h_3$ with a sample of 1–10 μm in particle size. As can be seen from this figure, the influence of inserted length is weak on the part of finer particles, but the inserted length greatly affects errors in measuring on the part of coarser particles. The ratio of errors in measuring in the coarser particle range is smaller when the inserted length is greater.

Figure 7:
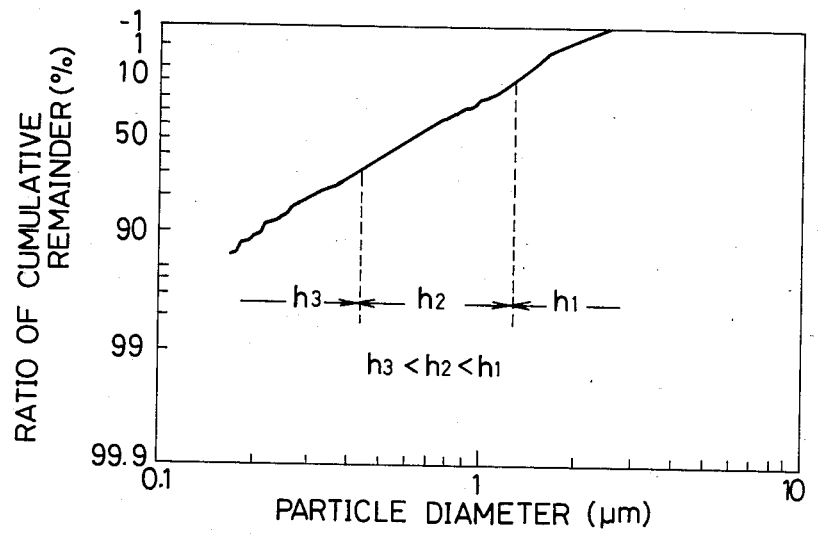
FIG. 7 is a diagram which shows another example thereof.

FIG. 7 shows a particle-size distribution curve for a representative powder, depicted (in percent) as the ratio of particles remaining in the sieve versus sieve mesh or opening diameter expressed in μm. This curve is divided into three segments to illustrate the portion of particle-size distribution that would be measured by each of three pairs of pressure transmitting tubes inserted at depths h1, h2 and h3 in cells containing identical samples of the powder.

By employing three pressure-detecting units 8 with couples of pressure transmitting tubes 5 and 6 which have inserted lengths H different among them and synthesizing the data from three pressure-detecting units, the measuring time as a whole could be decreased as a result of decrease in measuring time on the part of finer particles, without lowering the precision of measuring. For example, although the measuring needs about 3 hours when only one couple of pressure transmitting tubes is employed at inserted depth of $h_1$ for measuring down to the particles of 0.2 μm, the period of time for measuring all particles down to those of 0.2 μm in size is decreased by 50% when the finer particle side of the cumulative curve is determined with the use of another couple of pressure transmitting tubes inserted to the depth of $h_3$ shown in FIG. 3.

Moreover, yet another method for utilizing the apparatus according to this invention will be described in the following.

Different samples to be measured are introduced into the respective measuring cells 3 and couples of pressure transmitting tubes 5 and 6 are inserted to the same depth of $h_1$ in the respective measuring cells 3. The measurements are simultaneously conducted in the same manner as that mentioned above. By this procedure, multiple samples can be measured within a very short period of time under the same condition.

In addition, when these procedures are adopted, the calculation of a mean value which is usually conducted after measuring multiple samples successively can be easily performed. Further, when different samples are introduced in the respective measuring cells, data and the mean value as well as individual data of different samples can be obtained by only one measuring operation.

In the drawings and specification there have been set forth preferred embodiments of the invention, and although specific terms are employed, they are used in a generic and descriptive sense only and not for purposes of limitation.

What is claimed is:

1. An apparatus for measuring particle-size distribution of a powder which comprises: a measuring cell for receiving a suspension of particles to be measured, a rotor on which said measuring cell is mounted in a radial direction, a driving unit for rotating said rotor about an axis of rotation, a pair of parallel pressure transmitting tubes extending in a radial direction into said cell, each of said tubes having opposite tip and base ends, said tip ends of said pressure transmitting tubes inserted from the general direction of said axis into said measuring cell with said tip ends at individually different distances from said axis, and a pressure-detecting unit to which said base ends of said pressure transmitting tubes are secured, said pressure detecting unit having a pressure sensitive membrane between said base ends of said tubes for sensing the pressure difference between said tubes, said membrane being adjacent said axis of rotation of said rotor and lying in a plane extending radially thereof, said pressure-detecting unit being electrically connected with a measuring device.

2. The apparatus as defined in claim 1 wherein said axis is generally vertical.

3. The apparatus as defined in claim 1 wherein a pre-degassed liquid medium fills said pressure transmitting tubes.

4. The apparatus as defined in claim 1 wherein a silicone oil medium fills said pressure transmitting tubes.

5. An apparatus for measuring particle-size distribution of a powder which comprises: a rotor; a driving unit for rotating said rotor about an axis of rotation; and multiple measuring cells for receiving suspensions of particles to be measured arranged radially about said axis of rotation of said rotor; each of said cells having a corresponding pair of pressure transmitting tubes having opposite tip and base ends, said tip ends inserted from the general direction of said axis to an individually different distance from said axis in a measuring zone within the respective one of said cells and said base ends secured to a pressure-detecting unit that is electrically connected with a measuring device, wherein said measuring zone in each of said measuring cells is at an individually different distance from said axis than in the other of said cells and further wherein each said pressure-detecting unit to which said base ends of the respective said pressure transmitting tubes are secured has a pressure sensitive membrane between said base ends for sensing the pressure difference between said tubes, said membrane and said axis of rotation of said rotor are lying in one and the same plane and said membrane is adjacent said axis of rotation of said rotor.

* * * * *